(12) United States Patent
Harman

(10) Patent No.: US 9,545,378 B2
(45) Date of Patent: *Jan. 17, 2017

(54) AEROSOL VALVE

(71) Applicant: BTG International Limited, London (GB)

(72) Inventor: Anthony David Harman, Henley-on-Thames (GB)

(73) Assignee: BTG INTERNATIONAL LIMITED, London (GB)

( * ) Notice: Subject to any disclaimer, the term of this patent is extended or adjusted under 35 U.S.C. 154(b) by 904 days.

This patent is subject to a terminal disclaimer.

(21) Appl. No.: 13/718,639

(22) Filed: Dec. 18, 2012

(65) Prior Publication Data

US 2013/0189192 A1 Jul. 25, 2013

Related U.S. Application Data

(62) Division of application No. 12/083,871, filed as application No. PCT/GB2006/003916 on Oct. 20, 2006.

(60) Provisional application No. 60/728,809, filed on Oct. 21, 2005.

(51) Int. Cl.
| | |
|---|---|
| A61K 9/12 | (2006.01) |
| B65D 83/20 | (2006.01) |
| B65D 83/48 | (2006.01) |
| F16K 1/30 | (2006.01) |
| F16K 51/00 | (2006.01) |

(52) U.S. Cl.
CPC ............. *A61K 9/122* (2013.01); *B65D 83/20* (2013.01); *B65D 83/48* (2013.01); *F16K 1/303* (2013.01); *F16K 1/308* (2013.01); *F16K 51/00* (2013.01); *A61K 9/124* (2013.01)

(58) Field of Classification Search
CPC ........ A61K 9/122; A61K 9/12; B65D 83/14; Y10S 514/945; A61M 11/00; A61M 11/02; A61M 2202/03; F16K 1/303
See application file for complete search history.

(56) References Cited

U.S. PATENT DOCUMENTS

| 6,572,873 B1 * | 6/2003 | Osman ................. A61K 9/0019 424/423 |
| 2004/0056054 A1 * | 3/2004 | Ottolangui .......... A61M 15/009 222/544 |

FOREIGN PATENT DOCUMENTS

| EP | 1 455 128 A1 | 9/2004 | |
| FR | 2 852 301 A1 | 9/2004 | |
| GB | WO 2004062461 A2 * | 7/2004 | ........... A61K 9/0019 |
| WO | WO 00/72821 A1 | 12/2000 | |
| WO | WO 02/41872 A1 | 5/2002 | |
| WO | WO 02/051483 A1 | 7/2002 | |
| WO | WO 03/099681 A1 | 12/2003 | |
| WO | WO 2005/023678 A1 | 3/2005 | |
| WO | WO 2005/048976 A2 | 6/2005 | |
| WO | WO 2005/048977 A2 | 6/2005 | |
| WO | WO 2005/048983 A1 | 6/2005 | |
| WO | WO 2005/048984 A1 | 6/2005 | |
| WO | WO 2005/053776 A1 | 6/2005 | |

OTHER PUBLICATIONS

International Preliminary Report on Patentability; Date Mailed May 2, 2008; PCT International Application No. PCT/GB2006/003916; International Filing Date Oct. 20, 2006 (7 pgs).
BASF—Products & Markets—Ultrason® (PES and PSU). Technical Data retrieved Dec. 7, 2004.
Boedeker Plastics—Sortable Materials Properties Reference Table. Technical Data retrieved Dec. 7, 2004.
Express Pattern—Technical Data retrieved Oct. 7, 2004.
Feature Article—IMPACT which Test Use which Instrument to buy—10-01 Technical Data retrieved Oct. 7, 2004.
Fortron 0203hs—Web generated Technical Data retrieved Dec. 7, 2004.
Global Engineering Documents Family Search Results. Data Retrieved Dec. 7, 2004.
Goodfellow—Material Information. Data retrieved Dec. 7, 2004.
Izod Impact (Notched) ASTM D 256 ISO 180. Data Retrieved Oct. 12, 2004.
Materials—Paradigm Optics, Incorporated. Data Retrieved Oct. 7, 2004.
MatWeb—Online Material Data Sheet Hoechst Celazole PBI. Data Retrieved Dec. 10, 2004.
MatWeb—Online Material Data Sheet—polyimide rtp4200 unfilled. Data Retrieved Dec. 15, 2004.
MatWeb—Online Material Data Sheet—Radel A A100 Polyethersulfone. Data Retrieved Dec. 15, 2004.
MatWeb—Online Material Data Sheet—Radel R PPSU. Data Retrieved Dec. 15, 2004.
MatWeb—Online Material Data Sheet—RTP 2100 Polyetherimide. Data Retrieved Dec. 10, 2004.
MatWeb—Online Material Data Sheet—RTP Polyarylsulfone. Data Retrieved Dec. 10, 2004.
MatWeb—Online Material Data Sheet—Solvay Xydar G-930. Data Retrieved Dec. 15, 2004.
MatWeb—Online Material Data Sheet—Torlon 4203L PAI. Data Retrieved Dec. 15, 2004.

(Continued)

*Primary Examiner* — Mark V Stevens
(74) *Attorney, Agent, or Firm* — Nixon & Vanderhye P.C.

(57) ABSTRACT

Method for producing a microfoam suitable for use in scleropathy of blood vessels by introducing a physiologically acceptable blood-dispersible gas into a container holding an aqueous sclerosant liquid and releasing the mixture of blood-dispersible gas and sclerosant liquid such that, upon release of the mixture, the components of the mixture interact to form a microfoam. The container is provided with a steam-sterilizable aerosol valve having a valve body of polymeric material having an HDT (heat deflection temperature) at 1.8 MPa stress in the range of 200-275 °C.

10 Claims, 3 Drawing Sheets

(56) References Cited

OTHER PUBLICATIONS

MatWeb—Online Material Data Sheet—Ude PSU. Data Retrieved Dec. 15, 2004.
MatWeb—Online Material Data Sheet—Vectra 1300MT LCP. Data Retrieved Dec. 15, 2004.
MatWeb—Online Material Data Sheet—Victrex PEEK 150G. Data Retrieved Dec. 15, 2004.
MSDS PPSU 1000 EN—Data Retrieved Oct. 14, 2004.
Poly(ethersulfone) information and properties. Data Retrieved Dec. 10, 2004.
Polyetherimide information and properties. Data Retrieved Dec. 10, 2004.
Pomalux Interstate Plastics. Data Retrieved Dec. 15, 2004.
Radel A Polyethersulfone Radel R Polyphenysulfone Design Guide. Data Retrieved Aug. 25, 2004.
Radel offered by Craftech Industries. Data Retrieved Dec. 15, 2004.
RTP Company Product Data Sheet—Data Retrieved Dec. 7, 2004.
J. Muzzy, "2.3 Thermoplastics—Properties", offprint from "Comprehensive Composite Materials" edited by A. Kelly and C. Zwebwn, Elsevier Science (2000); see section 2.3.4.10, p. 12.
U.S. Department of Defense / Office of the Secretary of Defense Critical Technology Program, Militarily Critical Technologies List (MCTL), 1996, "Section 11—Materials Technology"; see table 11.5-1a, Structural Materials (High-Strength and High-Temperature) Militarily Critical Technology Parameters, p. 11-11.
Solvay Radel R Datasheet. Data Retrieved Oct. 17, 2004.
Supplier Data—Polyetherimide (EI) (Goodfellow). Daa Retrieved Dec. 15, 2004.
Thermal Property Data. Data Retrieved Dec. 15, 2004.
IAPD summary. Data Retrieved Oct. 17, 2004.

\* cited by examiner

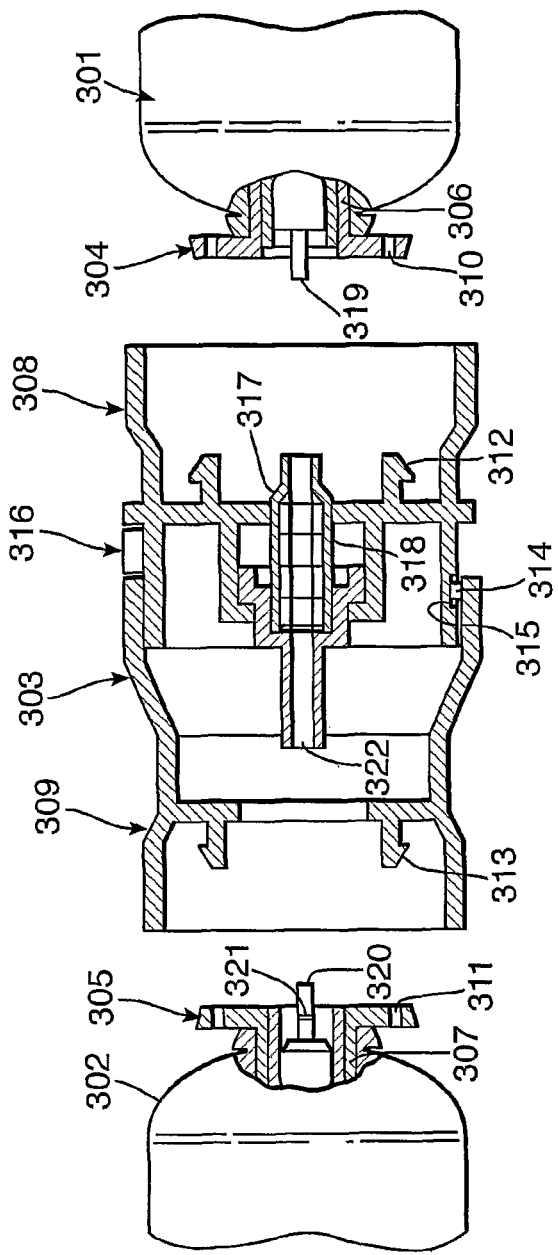

AEROSOL VALVE

This application is a divisional of application Ser. No. 12/083,871, filed May 2, 2008, which is a 371 of PCT/GB2006/003916, filed Oct. 20, 2005, which claims priority to Provisional Application No. 60/728,809 filed Oct. 21, 2005, the entire contents of each of which are hereby incorporated by reference.

This invention relates to a steam-sterilizable aerosol valve, particular one which may be used for the production of sclerosing foams useful in the therapy of varicose veins, and to an aerosol dispenser including such a valve.

WO 00/72821-A1 (BTG International Limited) provides a method and a number of different devices that are capable of producing a uniform injectable microfoam. The device may use a standard aerosol valve crimped into the top of a canister containing a sclerosing agent in solution. The pathway to the exterior of the housing includes one or more passages of diameter 0.1 μm to 30 μm. Passing a solution and gas mixture through these to reach the exterior of the device results in the injectable microfoam.

Various improved devices are shown in WO 02/41872-A1, WO 03/099681-A1, WO 2005/023678-A1, WO 2005/048976-A2, WO 2005/048977-A2, WO 2005/048983-A1, WO 2005/048984-A1 and WO 2005/053776-A1.

Various materials have been used generally for aerosol valve components. For example, EP 1455128-A1 (Scanferla) shows a guiding device for a valve stem comprising an annular body with a plurality of fins extending from it. These are preferably made of plastics material made of polyoxymethylene (POM), polyamide (PA), polyphenylene sulfide (PPS) or polyphenylene sulfone (PPSU). The use of such a material is said to give a self-lubricating device.

Most thermoplastics used up to now for the moulding of aerosol valve components, for example polyamide 6/6 (PA 6/6), polypropylene (PP) and polyoxymethylene (POM), have heat distortion temperatures below common steam sterilization temperatures of 121-125° C. However, conventional aerosol valve design requires that the plastics housing component exerts a constant reactive elastic force against the crimped metal mounting cup to maintain a gas-tight seal at the critical stem gasket.

We have noted that steam sterilization may cause the crimp between housing and mounting cup to become loose, through thermal expansion, water uptake and stress relaxation in the plastics material. This can cause the valve to leak as the stem gasket loses its precompression between housing and mounting cup.

It might be predicted that changing to a material that has an HDT (heat deflection temperature) of 130° C. or more, such as polycarbonate (PC) and polysulfone (PSU), would be sufficient to avoid this problem. However, in practice we have determined this not to be the case.

When an aerosol dispenser is used for the production of sclerosing foams, useful in the therapy of varicose veins, control over the gas paths inside the dispenser is crucial. When the sclerosing foam is a microfoam, it is preferable that the sclerosant microfoam should be composed of spherical bubbles (Kugelschaum) of the correct density to allow the microfoam to flow through a hypodermic needle without significant loss of structure or properties. In the production of such a microfoam, even if the stem gasket seal remains effective in preventing loss of pressurized contents to atmosphere from the aerosol container, the loss of crimp force between housing and mounting cup can create an additional gas path from the pressurized canister headspace to the valve metering chamber. This may result in a sclerosing microfoam having a low density and a dry, polyhedral-celled structure that does not have the required "Kugelschaum" properties to survive injection through a narrow needle or cannula at the required injection speeds.

It has now been surprisingly discovered that changing the plastics material to one that has an HDT (heat deflection temperature) of 200° C. or more, such as polyphenylsulfone (PPSU), polyetherimide (PEI) and polyetheretherketone (PEEK), will avoid this unwanted effect.

Accordingly the first aspect of the present invention provides a steam-sterilizable aerosol valve having a valve body of polymeric material, characterized in that the valve body comprises a material having an HDT (heat deflection temperature) at 1.8 MPa stress in the range of 200-275° C.

We believe that the reason for such an excessive headroom of HDT being needed is to avoid any significant stress relaxation in the plastics housing during autoclaving (generally 125° C. for 30 minutes), and during the following slow cool-down to room temperature. Otherwise the rubber stem gasket may lose the 50% compression that is usually applied in crimping and the seal is compromised. When the aerosol valve is incorporated in a microfoam dispensing system and is terminally sterilized by steam to allow production of a sterile sclerosing microfoam, it thus can be made to give a microfoam of spherical bubbles (Kugelschaum) of the correct density to allow the microfoam to flow through a hypodermic needle without significant loss of structure or properties.

The element of the valve that crucially needs to be made of the high HDT material is the valve body. However, there might be problems with distortion under heat of the stem valve and valve insert if they are not made of the same material as the valve body. Thus preferably the stem valve and valve insert are also made of a material having an EDT (heat deflection temperature) at 1.8 MPa stress in the range of 200-275° C. Ideally the stem valve and valve insert are made of the same material as the valve body. The elements can thus be prestressed against each other and against the metal components during and after terminal sterilization of the assembled aerosol valve.

The HDT of the valve body at 1.8 MPa stress is preferably in the range of 200-250° C. More preferably the EDT is in the range of 200-210° C., and most preferably in the range of 204-207° C.

The glass transition temperature (Tg) of the valve body material is preferably in the range of 200-330° C. More preferably Tg is in the range of 210-230° C., and most preferably Tg is 220° C.

The plastics material chosen for steam sterilized aerosol valves should ideally also be resistant to swelling with water, and to hydrolysis at the elevated temperatures. The moisture absorption (after 24 hours in moist air) of the valve body material is preferably below 0.75%. More preferably the moisture absorption is below 0.6%, and most preferably the moisture absorption is below 0.4%.

The water take-up at saturation in liquid of the valve body material is preferably below 3%. More preferably the water take-up is below 2.5%, and most preferably the water take-up is below 1.5%.

Ejecting moulded valve parts out of the valve mould can involve bump-offs, snap-fit features and other fixation features that are difficult to eject and which stress the material. The valve body material should therefore ideally have good craze resistance. Thus a high impact strength is desirable. The Izod impact strength of the valve body material is preferably 0.8 J cm$^{-1}$ or greater. More preferably the Izod impact strength is above 1.0 J cm$^{-1}$, and most preferably the Izod impact strength is above 5.0 J cm$^{-1}$.

A moderately low tensile stiffness is also desirable. The tensile stiffness of the valve body material is preferably below 4.0 GPa. More preferably the tensile stiffness is below 3.0 GPa, and most preferably the tensile stiffness is below 2.5 GPa.

Suitable valve body materials thus include the following:

| Polymer | Heat deflection temperature at 1.8 MPa (° C.) | Glass transition temp (° C.) | Moisture absorption (after 24 hours in moist air) | Water take-up at saturation in liquid | Izod impact strength (J cm$^{-1}$) | Tensile stiffness (GPa) |
|---|---|---|---|---|---|---|
| PEI | 200 | 216 | 0.25% | 1.3% | 0.534 | 3.31 |
| PES | 204 | 220 | 0.54% | 2.1% | 0.9 | 2.65 |
| PPSU | 207 | 220 | 0.37% | 1.1% | 6.9 | 2.34 |
| PI | 241 | 330 | 0.24% | 2.9% | 1.12 | 2.41 |
| LCP | 265 | >300 | 0.03% | 0.1% | 7 | 12.2 | where PEI is polyetherimide, PES polyethersulfone, PPSU polyphenylsulfone, PI polyimide and LCP liquid crystal polymer. Using such materials gives an aerosol valve with good resistance to hydrolysis and autoclavability.

Even a highly crystalline plastics material such as LCP can be used, as long as the crystal structure is maintained at and above autoclave temperatures. The properties listed above for LCP refer to a 40% mineral loaded grade of LCP (Zenite™ FG177340, Du Pont), as LCP is not normally available commercially as a homo-polymer.

PPSU has however been found to be the best choice of plastics material, having an HDT of 207° C. at 1.8 MPa stress. PPSU has the necessary chemical and hydrolytic resistance and easily withstands being held for about 40 minutes at a temperature of 130° C. in an autoclave.

Polyphenylsulfone (PPSU) represents a polymer with the repeating unit:

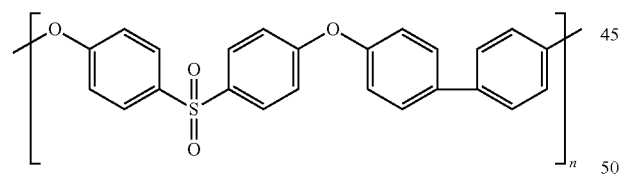

This compound may be regarded as a copolymer between compounds of formula:

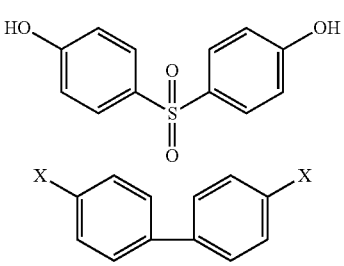

where X is fluorine or chlorine. PPSU polymer is offered in several grades, such as the coloured grade Radel™ R 5100. Preferred is Radel™ R 5000, the general purpose transparent grade, from Solvay Advanced Polymers.

The same manufacturer's polyethersulfone (PES), such as the grade Radel™ A-100, also gives good results. This has the repeating unit:

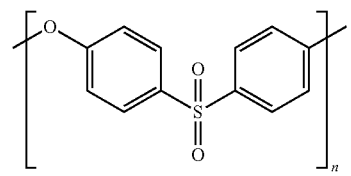

with a low level of polyetherethersulfone (PEES):

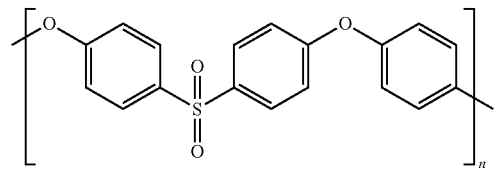

Thus a preferred valve body comprises a polymer of formula:

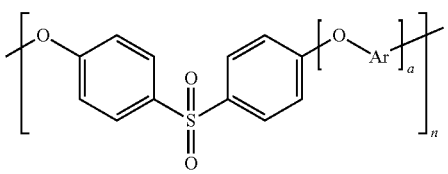

where a is 0 or 1 and Ar is 1,4-phenylene or 4,4'-biphenylene. In the case where a is 1, such a compound may be regarded as a copolymer between compounds of formula:

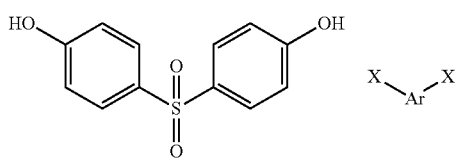

where Ar is as defined above and X is fluorine or chlorine.

In contrast, we have found the following to be unsuitable:

| Polymer | | Heat deflection temperature at 1.8 MPa (° C.) |
|---|---|---|
| PPS | polyphenylene sulfide | 120 |
| PEEK | polyetheretherketone | 160 |
| PSU | polysulfone | 174 |
| PAI | polyamide-imide | 278 |
| PBI | polybenzimidazole | 427 |

The aerosol valve may be attached to a dip tube made of polypropylene or other soft plastic capable of maintaining its original shape at autoclave temperatures. This can form a seal against the grooves and ridges of the tailpiece of the valve body when assembled by the conventional push-fit method.

The present invention may be used with any of the devices disclosed in WO 00/72821-A1 (BTG International Limited) provides a method and a number of different devices that are capable of producing a uniform injectable microfoam. Various improved devices are shown in WO 02/41872-A1, WO 03/099681-A1, WO 2005/023678-A1, WO 2005/048976-A2, WO 2005/048977-A2, WO 2005/048983-A1, WO 2005/048984-A1 and WO 2005/053776-A1. All of these are incorporated herein by reference.

Thus in a second aspect the present invention provides a device for producing a microfoam suitable for use in scleropathy of blood vessels, including a steam-sterilizable aerosol valve having a valve body of polymeric material, characterized in that the valve body comprises a material having an HDT (heat deflection temperature) at 1.8 MPa stress in the range of 200-275° C.

The device may comprise a housing in which is situated a pressurizable chamber containing a solution of the sclerosing agent in a physiologically acceptable solvent; a pathway with one or more outlet orifices by which the solution may pass from the pressurizable chamber to the exterior of the device through said one or more outlet orifices and a mechanism by which the pathway from the chamber to the exterior can be opened or closed such that, when the container is pressurized and the pathway is open, fluid will be forced along the pathway and through the one or more outlet orifices;

said housing incorporating an inlet for the admission of a pressurized source of physiologically acceptable gas that is dispersible in blood; the gas being in contact with the solution on activation of the mechanism such as to produce a gas-solution mixture;

said pathway to the exterior of the housing including one or more foaming elements.

The foaming element(s) may comprise one or more passages of cross sectional dimension, preferably diameter, 0.1 µm to 30 µm, through which the solution and gas mixture is passed to reach the exterior of the device, said passing of said mixture through the passages forming a microfoam of from 0.07 to 0.19 g/ml density and of half-life at least 2 minutes.

In a third aspect the present invention provides a method for producing a microfoam suitable for use in scleropathy of blood vessels, comprising introducing a physiologically acceptable blood-dispersible gas into a container holding an aqueous sclerosant liquid and releasing the mixture of blood-dispersible gas and sclerosant liquid, whereby upon release of the mixture the components of the mixture interact to form a microfoam, the container being provided with a steam-sterilizable aerosol valve having a valve body of polymeric material, characterized in that the valve body comprises a material having an HDT (heat deflection temperature) at 1.8 MPa stress in the range of 200-275° C.

The sclerosant liquid utilized in the invention may be any of those discussed in WO 00/72821-A1 and WO 02/41872-A1. Preferably the sclerosant liquid is a solution of polidocanol or sodium tetradecyl sulfate in an aqueous carrier, e.g. water, particularly in a saline. More preferably the solution is from 0.25 to 5% vol/vol polidocanol, preferably in sterile water or a physiologically acceptable saline, e.g. in 0.5 to 2% vol/vol saline. More preferably still, the concentration of polidocanol is from 0.5 to 5% vol/vol in the liquid, preferably 0.5 to 3% vol/vol polidocanol and most preferably being 1% vol/vol in the liquid.

The sclerosant may also contain additional components, such as stabilizing agents, e.g. foam stabilizing agents, e.g. such as glycerol. Addition of glycerol to the aforesaid sclerosant imparts a longer half-life to the resultant foam. Further components may include alcohols such as ethanol. Even though this may reduce foam stability, inclusion of a few percent of ethanol is thought to aid in solubilizing low-molecular-weight oligomers of polidocanol and also prevent degradation of the polidocanol.

The water or saline also may contain 2-5% vol/vol physiologically acceptable alcohol, e.g. ethanol. The polidocanol solution is preferably phosphate buffered to pH 6.7-7.3.

For the purpose of this application terms have the following definitions. Physiologically acceptable blood-dispersible gas is a gas that is capable of being substantially completely dissolved in or absorbed by blood. A sclerosant liquid is a liquid that is capable of sclerosing blood vessels when injected into the vessel lumen. Scleropathy or sclerotherapy relates to the treatment of blood vessels by injection of a sclerosing agent to eliminate them. Half-life of a microfoam is the time taken for half the liquid in the microfoam to revert to unfoamed liquid phase, under the influence of gravity, and at a defined temperature.

The mixture of blood-dispersible gas and sclerosant liquid is preferably pressurized to a pre-determined level. Preferred pressures are in the range 800 mbar to 4.5 bar gauge (1.8 bar to 5.5 bar absolute). Pressures in the range of 1 bar to 2.5 bar gauge have been found to be particularly effective.

Preferably the microfoam is such that less than 20% of the bubbles are less than 30 µm diameter, greater than 75% are between 30 and 280 µm diameter, less than 5% are between 281 and 500 µm diameter, and there are substantially no bubbles greater than 500 µm diameter.

Preferably the gas/liquid ratio in the mix is controlled such that the density of the microfoam is 0.07 g/ml to 0.19 g/ml, more preferably 0.10 g/ml to 0.15 g/ml.

Preferably the microfoam has a half-life of at least 2 minutes, more preferably at least 2.5 minutes. The half-life may be as high as 1 or 2 hours or more, but is preferably less than 60 minutes, more preferably less than 15 minutes and most preferably less than 10 minutes.

As the production of sclerosing foams for the therapy of varicose veins is a medical end use, it is essential that the materials in contact with the sclerosing foam and its components should have FDA regulatory approvals, and the materials will also be listed in a Drug Master File (DMF) for submission to the Food and Drug Administration (FDA).

The present invention will now be described further by way of illustration only by reference to the following Figures and Examples. Further embodiments falling within the scope of the invention will occur to those skilled in the art in the light of these.

BRIEF DESCRIPTION OF THE DRAWINGS

FIG. 3 shows a shows a cross-sectional view of a device comprising a container provided with engaging means and a mesh stack shuttle according to the invention, as disclosed in WO 02/41872-A1 and further described in Example 3 below.

EXAMPLES

Example 1

Exploded Diagram of an Aerosol Valve

Figure 1:
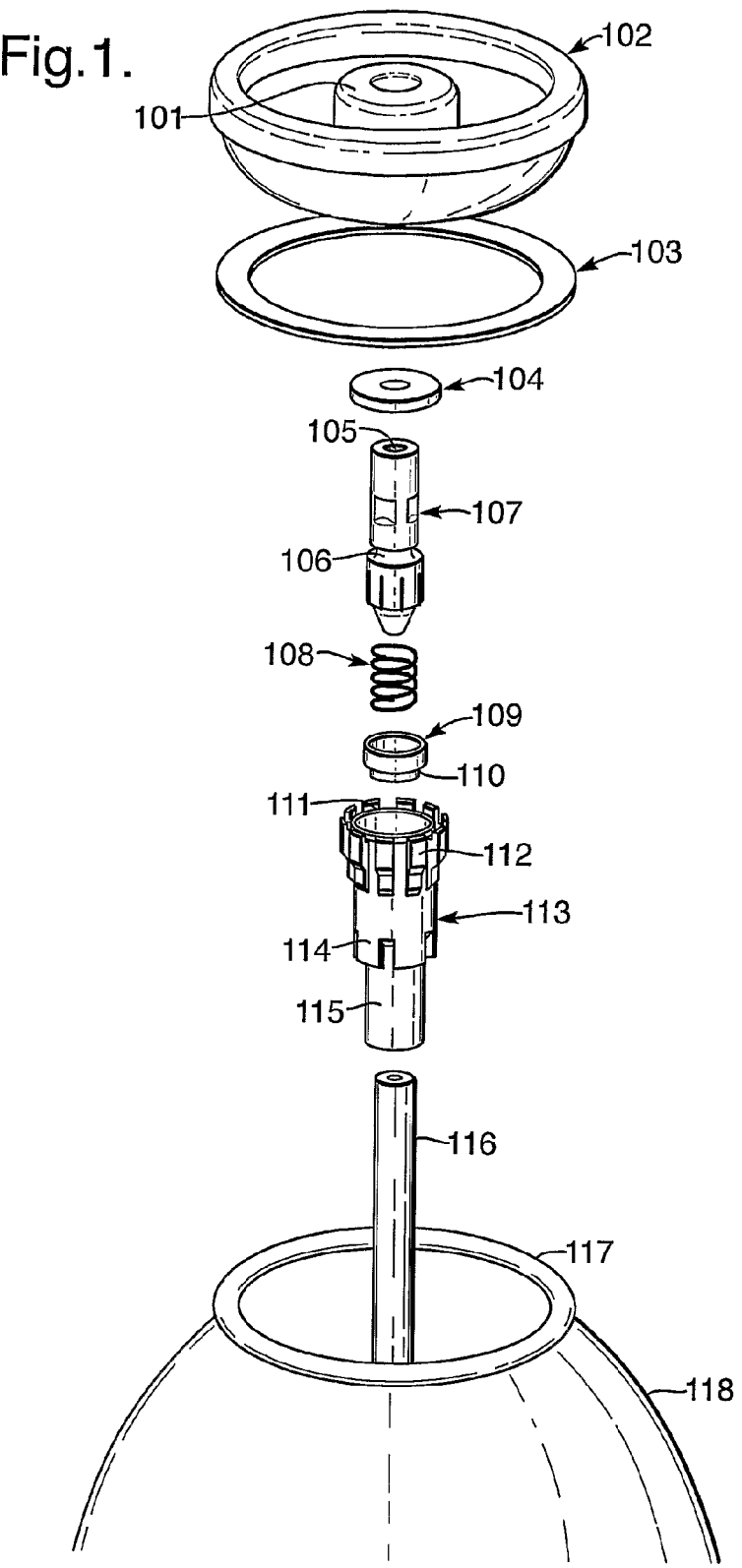
FIG. 1 shows an exploded diagram of an aerosol valve in situ in an aerosol dispenser, as further described in Example 1 below.

An exploded diagram of an aerosol valve in situ in an aerosol dispenser is shown in FIG. 1.

The stem gasket (104) is pre-assembled onto the stem (107) so that it seals against the seat for the stem gasket (106) on the stem and covers a small side hole in the stem that leads to the stem orifice (105), which acts as an outlet for the contents of the canister. A stainless steel spring (108) is then prefitted to the base of the stem moulding.

The insert (109) is pre-assembled into the valve body (113) and sealingly seats the gas channels formed on the bottom of the insert (110) against the internal flat base of the valve body (113) to create two internal gas metering slots that are in communication with the external slots (114) on the valve body (113), thereby creating a metered gas path from the headspace of the canister to the inside of the valve body (113) when the valve is later clinched onto the canister.

The metal mounting cup (102) is prefitted with a cup gasket (103) to form a gas-tight seal against the canister curl (117) when the assembled valve is clinched to the canister by standard industry means.

The subassemblies described above are then crimped together using a standard pedestal crimping tool to make the fully assembled valve. The stem gasket (104) is compressed by 50% in thickness by the crimping procedure, and the pedestal of the mounting cup (101) is deformed during crimping to engage and retain on the castellations (112) on the external surface of the valve body (113).

A polypropylene dip tube (116) is push-fitted into sealing engagement with the tailpiece of the valve body (115) to complete the valve assembly.

The canister (118) is part-filled with 15 ml of 1% polidocanol solution, and the atmospheric air inside the canister (118) is purged with the desired gas mixture before the assembled valve and dip tube are clinched onto the canister curl (117) by use of conventional clinching equipment to make a gas-tight seal between the assembled valve and the canister. The canister (118) is then pressurized to the desired working pressure (using the desired gas mixture) by gassing through the stein orifice (105).

The entire pressurized unit of canister, clinched valve and contents is then sterilized at 121-125° C. for 30 minutes in a suitable autoclave unit and allowed to cool to room temperature. It is crucial that the pedestal crimp formed before autoclaving remains tight during and after autoclaving. This is achieved by choosing the moulding material of the valve body (113) to have a sufficiently high heat distortion temperature to avoid stress relaxation in the castellation area of the moulded valve body (112), in order to avoid a gas leak path developing between the bottom of the stem gasket (104) and the valve housing ridge (111) which it is compressed against in the assembled state.

A small metering hole (not shown) at the top of the tailpiece of the valve body (115) meters the liquid into the valve body (113) from the bottom of the canister (118) via the dip tube (116) and mixes the metered liquid with the gas entering the valve body through the gas slots on the base of the insert to form a crude foam with large bubbles. This crude foam is homogenized and conditioned to yield microfoam suitable for use in sclerotherapy by subsequent passage through a mesh stack shuttle (not shown) that sealingly engages with the stem valve outlet (105).

When the stem valve is depressed by more than approximately 1 mm through application of external force, the stem gasket deforms away from the side hole in the stem gasket seat area, opening a path between the canister and the external environment. When this external force is released, the spring (108) returns the stem to its fully closed position.

Example 2

Pre-Pressurized Container

Figure 2:
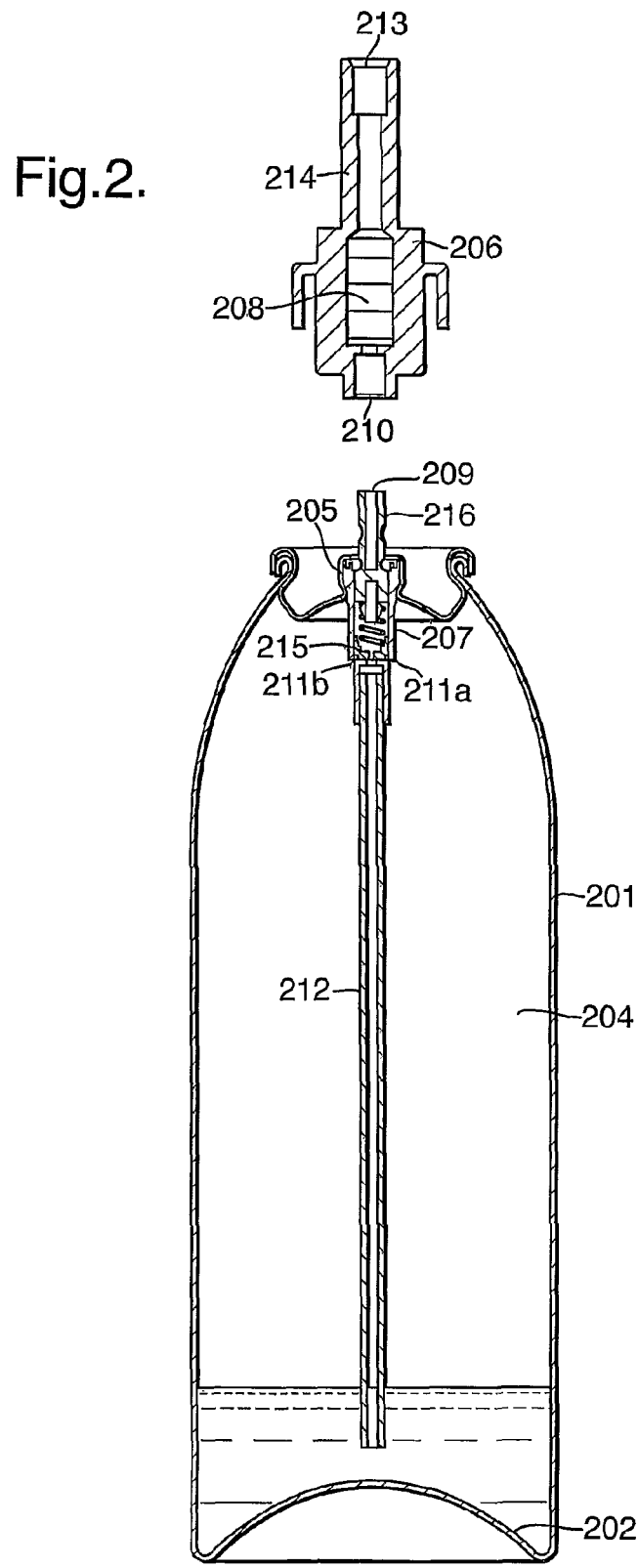
FIG. 2 shows a cross-sectional view of a pre-pressurized container for the generation of therapeutic microfoam according to the invention, as further described in Example 2 below.

A typical apparatus for the generation of therapeutic microfoam according to the invention, is shown in FIG. 2.

The canister has an aluminium wall (201), the inside surface of which is coated with an epoxy resin. The bottom of the canister (202) is domed inward. The canister inner chamber (204) is pre-purged with 100% oxygen for 1 minute, containing 15 ml of a 1% vol/vol polidocanol/20 mmol phosphate buffered saline solution/4% ethanol, then filled with oxygen at 2.7 bar gauge (1.7 bar over atmospheric).

A typical gas mixture is 3% He, and between 25 and 35% $CO_2$, with the balance $O_2$ as a final gas mixture at approx. 3.5 bar absolute.

A standard 1 inch diameter aerosol valve (205) is clinched on to the top of the canister after sterile part filling with the solution and may be activated by push-fitting the inlet (210) of the mesh stack connector (206) into sealing engagement with the outlet (209) of the stem valve (216). Activation of the valve (205) is achieved by pushing down on the mesh stack shuttle (206) to depress the engaged stem valve (216) and thereby release the contents of the aerosol canister (201) via an outlet nozzle (213) sized to engage a Luer fitting of a syringe or multi-way connector (not shown). This mesh stack shuttle (206) mounts four Nylon 66 meshes held in high density polyethylene (HDPE) rings (208), all within an open-ended polypropylene casing (214). These meshes have diameter of 6 mm and have a 14% open area made up of 20 μm pores, with the meshes spaced 3.5 mm apart.

The valve (205) comprises a housing (207) which mounts the dip tube (212) and includes gas receiving holes (211a, 211b) which admit gas from chamber (204) into the flow of liquid which rises up the dip tube on operation of the mesh stack shuttle (206) to open the valve (205). These are conveniently defined by an Ecosol™ device provided by Precision Valve, Peterborough, UK, provided with an insert (215). Holes (211a, 211b) have cross-sectional area such that the sum total ratio of this to the cross-sectional area of the liquid control orifice at the base of the valve housing (at the top of the dip tube) is controlled to provide the required gas/liquid ratio.

A valve body (207) of polyphenyl sulfone (PPSU) is provided. The stem valve (216) and valve insert (215) are also made of PPSU.

Example 3

Container with Engaging Means and Mesh Stack Shuttle

A device comprising a container provided with engaging means and a mesh stack shuttle according to the invention, as disclosed in WO 02/41872-A1, is shown in FIG. 3. The device comprises a low pressure container (301) for an aqueous sclerosant liquid and an unreactive gas atmosphere, a container (302) for a physiologically acceptable blood-dispersible gas and an engaging means comprising a connector (303).

The container (302) for a physiologically acceptable blood-dispersible gas is charged at 5.8 bar absolute pressure with oxygen, whereas the container (301) is charged with carbon dioxide. Container (302) is used to pressurize container (301) at the point of use to approx. 3.5 bar absolute and is then discarded, just before the microfoam is required. The two containers will thus be referred to hereinafter as the PD [polidocanol] can (301) and the $O_2$ can (302).

Each of the cans (301, 302) is provided with a snap-fit mounting (304, 305). These may be made as identical mouldings. The snap-fit parts (304, 305) engage the crimped-on mounting cup (306, 307) of each can (301, 302) with high frictional force. The connector is made in two halves (308, 309), and the high frictional force allows the user to grip the two connected cans (301, 302) and rotate the connector halves (308, 309) relative to each other without slippage between connector (303) and cans. Each of these can mountings (306, 307) has snap-fit holes (310, 311) for engaging mating prongs (312, 313) which are on the appropriate surfaces of the two halves (308, 309) of the connector.

The connector (303) is an assembly comprising a number of injection mouldings. The two halves (308, 309) of the connector are in the form of cam track sleeves which fit together as two concentric tubes. These tubes are linked by proud pins (314) on one half that engage sunken cam tracks (315) on the other half. The cam tracks have three detented stop positions. The first of these detents is the stop position for storage. An extra security on this detent is given by placing a removable collar (316) in a gap between the end of one sleeve and the other. Until this collar (316) is removed it is not possible to rotate the sleeves past the first detent position. This ensures against accidental actuation of the connector.

The cam track sleeves (308, 309) are injection moulded from PSU (polysulfone) or ABS as separate items, and are later assembled so that they engage one another on the first stop of the detented cam track. The assembled sleeves are snap-fitted as a unit onto the $O_2$ can (302) mounting plate (305) via four locating prongs. The security collar is added at this point to make an $O_2$ can subassembly.

The connector (303) includes in its interior a series of foaming elements comprising a mesh stack shuttle (317) on the connector half (308) adjacent to the PD can (301). The mesh stack shuttle (317) is comprised of four injection moulded disk filters with mesh hole size of 20 µm and an open area of approx. 14%, and two end fittings, suitable for leak-free connection to the two canisters. These elements are pre-assembled and used as an insert in a further injection moulding operation that encases them in an overmoulding (318) that provides a gas-tight seal around the meshes, and defines the outer surfaces of the mesh stack shuttle. The end fittings of the stack (317) are designed to give gas-tight face and/or rim seals against the stem valves (319, 320) of the two cans (301, 302) to ensure sterility of gas transfer between the two cans.

The mesh stack shuttle (317) is assembled onto the PD can valve (319). The PD can (301) and attached shuttle (317) are offered up to the connector (303) and the attached $O_2$ can (302), and a sliding fit made to allow snap-fitting of the four locating prongs (312) on the PD can side of the connector (303) into the mating holes (310) in the mounting plate (304) on the PD can (301). This completes the assembly of the system. In this state, there is around 2 mm of clearance between the stem valve (320) of the $O_2$ can (302) and the point at which it will form a seal against a female Luer outlet from the stack.

When the security collar (316) is removed, it is possible to grasp the two cans (301, 302) and rotate one half of the connector (303) against the other half to engage and open the $O_2$ can valve (320).

As the rotation of the connector (303) continues to its second detent position, the PD can valve (319) opens fully. The gas flow from the $O_2$ can (302) is restricted by a small outlet hole (321) in the stem valve (320). It takes about 45 seconds at the second detent position for the gas pressure to (almost) equilibrate between the two cans to a level of 3.45 bar±0.15 bar.

After the 45 second wait at the second detent position, the connector (303) is rotated further to the third detent position by the user. At this position, the two cans (301, 302) can be separated, leaving the PD can (301) with half (308) of the connector and the shuttle assembly (317) captive between the connector and the PD can. The $O_2$ can (302) is discarded at this point.

A standard 1 inch diameter aerosol valve (319) (Precision Valve, Peterborough, UK) is clinched on to the top of the PD can (301) before or after filling with the solution and may be activated by depressing the mesh stack shuttle (317), which functions as an aerosol valve actuator mechanism, to release the contents via an outlet nozzle (322) sized to engage a Luer fitting of a syringe or multi-way connector (not shown). The aerosol valve (319) has a valve body (not shown) of polyphenyl sulfone (PPSU). The stem valve and valve insert are also made of PPSU.

Example 4

Alternative Polymer Materials

The resistance to hydrolysis and autoclavability of a number of materials was evaluated by moulding components and assembling them to make functioning valves. Table 1 shows the properties observed with polymers of the invention, whereas Table 2 shows some comparative polymers. Izod impact strength refers to the value measured according to the ASTM D256 and ISO 180 procedure, a swinging pendulum test, and is defined as the kinetic energy needed to initiate fracture and continue the fracture until the specimen is broken.

When the valve body is made of unsuitable material, the failure mode in autoclaving is an easing of the crimp stress between valve castellations and the pedestal (centre bump) of the aluminium mounting cup. At 125° C., the contact stress eases off as the plastic creeps or stress relaxes against unyielding metal. As the valve cools down after autoclaving, thermal contraction of the plastic eases it further out of contact, and the water content of the plastic decreases to equilibrium in 100% relative humidity, further shrinking the plastic away from the mounting cup to give eventually a leak path for headspace gases to enter the valve. In extreme cases the valve falls apart at the pedestal crimp, as the internal spring is always compressed in an assembled valve and drives the valve body away from the mounting cup if the crimp fails.

On the other hand, using a material of the invention gives good results. PPSU especially has been found to have the ability to survive up to two thousand steam sterilization cycles without significant degradation of properties or appearance. The sulfone group, in conjunction with the biphenylene unit that elevates the impact strength, evidently imparts great stiffness and toughness to the polymer chain, giving a heat deflection temperature value that is normally only seen with rather brittle materials.

TABLE 1

Polymers of the invention

| Polymer | Polymer grade | Heat deflection temperature at 1.8 MPa (° C.) | Glass transition temp (° C.) | Moisture absorption (after 24 hours in moist air) | Water take-up at saturation in liquid | Izod impact strength (J cm$^{-1}$) | Tensile stiffness (GPa) | Hydrolytic resistance and autoclavability |
|---|---|---|---|---|---|---|---|---|
| PEI | RTP 2100 unfilled | 200 | 216 | 0.25% | 1.3% | 0.534 | 3.31 | OK, but notch sensitive, so prone to stress crack. |
| PES | Solvay Radel ™ A A-100 | 204 | 220 | 0.54% | 2.1% | 0.9 | 2.65 | Stable, good |
| PPSU | Solvay Radel ™ R 5000 | 207 | 220 | 0.37% | 1.1% | 6.9 | 2.34 | Very stable, excellent |
| PI | RTP 4200 unfilled | 241 | 330 | 0.24% | 2.9% | 1.12 | 2.41 | OK, OK |
| LCP | Du Pont Zenite ™ FG77340 | 265 | >300 | 0.03% | 0.1% | 7.0 | 12.2 | Acceptable, OK |

PEI = polyetherimide
PES = polyethersulfone
PPSU = polyphenylsulfone
PI = polyimide
LCP = liquid crystal polymer

TABLE 2

Comparative polymers

| Polymer | Polymer grade | Heat deflection temperature at 1.8 MPa (° C.) | Glass transition temp (° C.) | Moisture absorption (after 24 hours in moist air) | Water take-up at saturation in liquid | Izod impact strength (J cm$^{-1}$) | Tensile stiffness (GPa) | Hydrolytic resistance and autoclavability |
|---|---|---|---|---|---|---|---|---|
| PPS | Ticona Fortron ™ 0203B6 or 9203HS | 120 | 90 | 0.02% | 0.03% | 0.3 (brittle) | 4.2 | OK, but not autoclavable at 125° C. |
| PEEK | Victrex 143 | 160 | 143 | ?0.5% | 0.5% | 0.6 | 3.5 | OK, but yield stress at pedestal crimp of valve too low at 125° C. |
| PSU | Solvay Udel ™ 1700 | 174 | 190 | 0.3% | 0.8% | 0.7 | 2.5 | Stable, but yield stress at pedestal crimp of valve too low at 125° C., stress cracking also an issue |
| PAI | Solvay Torlon ™ 4203L | 278 | 275 | ?1.7% (unacceptable) | ? | 1.33 | 4.1 | Poor, unsuitable |
| PBI | Hoechst Celanese Celazole ™ PBI 399 | 427 | 399 | 0.4% | 5% | 0.27 (brittle) | 5.86 | Poor, unsuitable |

PPS = polyphenylene sulfide
PEEK = polyetheretherketone
PSU = polysulfone
PAI = polyamide-imide
PBI = polybenzimidazole

The invention claimed is:

1. A method for producing a microfoam suitable for use in scleropathy of blood vessels, comprising introducing a physiologically acceptable blood-dispersible gas into a container holding an aqueous sclerosant liquid and releasing the mixture of blood-dispersible gas and sclerosant liquid, whereby upon release of the mixture the components of the mixture interact to form a microfoam, the container being provided with a steam-sterilizable aerosol valve having a valve body of polymeric material, wherein the valve body consists of a polymeric material having an HDT (heat deflection temperature) at 1.8 MPa stress in the range of 200-275° C.

2. A method as claimed in claim 1, wherein the sclerosant liquid is a solution of polidocanol or sodium tetradecyl sulfate in an aqueous carrier.

3. A method as claimed in claim 2, wherein the solution is from 0.25 to 5% vol/vol polidocanol.

4. A method as claimed in claim 1, wherein the mixture of blood-dispersible gas and sclerosant liquid is pressurized to a pre-determined level in the range 800 mbar to 4.5 bar gauge (1.8 bar to 5.5 bar absolute).

5. A method as claimed in claim 4, wherein the pressure is in the range of 1 bar to 2.5 bar gauge.

6. A method as claimed in claim 1, wherein the microfoam is such that less than 20% of the bubbles are less than 30 μm diameter, greater than 75% are between 30 and 280 μm diameter, less than 5% are between 281 and 500 μm diameter, and there are substantially no bubbles greater than 500 μm diameter.

7. A method as claimed in claim 1, wherein the gas/liquid ratio in the mix is controlled such that the density of the microfoam is 0.07 g/ml to 0.19 g/ml.

8. A method as claimed in claim 1, wherein the microfoam has a half-life of at least 2 minutes.

9. A method as claimed in claim 1, wherein the steam-sterilizable aerosol valve comprises a valve body that consists of polyphenylsulphone (PPSU).

10. A method as claimed in claim 1, wherein the steam-sterilizable aerosol valve comprises a valve body, a valve insert and a stem valve that consist of polyphenylsulphone (PPSU).

* * * * *